(12) United States Patent
McQuarrie

(10) Patent No.: US 6,355,181 B1
(45) Date of Patent: Mar. 12, 2002

(54) METHOD AND APPARATUS FOR MANUFACTURING A MICROMECHANICAL DEVICE

(75) Inventor: Andrew Duncan McQuarrie, San Jose, CA (US)

(73) Assignee: Surface Technology Systems plc, Newport (GB)

( * ) Notice: Subject to any disclaimer, the term of this patent is extended or adjusted under 35 U.S.C. 154(b) by 0 days.

(21) Appl. No.: 09/423,979

(22) PCT Filed: Mar. 16, 1999

(86) PCT No.: PCT/GB99/00774

§ 371 Date: Nov. 17, 1999

§ 102(e) Date: Nov. 17, 1999

(87) PCT Pub. No.: WO99/49506

PCT Pub. Date: Sep. 30, 1999

(30) Foreign Application Priority Data

Mar. 20, 1998 (GB) .............................. 9805927
Mar. 4, 1999 (GB) .............................. 9904925

(51) Int. Cl.⁷ ............................. H01L 21/00; B44C 1/22
(52) U.S. Cl. ............................. 216/2; 216/11; 216/58; 216/79; 438/706; 438/714; 438/734; 438/739
(58) Field of Search ................. 216/2, 58–67, 216/79, 11; 156/345, 345 P; 438/706, 714, 719, 734, 735, 739

(56) References Cited

U.S. PATENT DOCUMENTS

| 4,190,488 A | 2/1980 | Winters |
| 4,478,677 A | 10/1984 | Chen et al. |
| 5,312,509 A | 5/1994 | Eschbach |
| 5,316,979 A | 5/1994 | MacDonald et al. |
| 5,340,437 A | 8/1994 | Erk et al. |
| 5,426,070 A | * 6/1995 | Shaw et al. .................... 216/2 |
| 5,658,417 A | 8/1997 | Watanabe et al. |

FOREIGN PATENT DOCUMENTS

| DE | 41 41 045 C1 | 12/1992 |
| EP | 0 729 175 A1 | 8/1996 |
| EP | 0 822 584 A2 | 2/1998 |
| WO | WO 96/23229 | 8/1996 |

OTHER PUBLICATIONS

D.E. Ibbotson et al., "Plasmaless dry etching of silicon with fluorine–containing compounds." J. Appl. Phys. 56 (10), Nov. 15, 1984, pp. 2939–2941.

Floy I–Jung Chang, "Xenon Difluoride Etching of Silicon for MEMS," Abstract, search.

\* cited by examiner

*Primary Examiner*—William A. Powell
(74) *Attorney, Agent, or Firm*—Volentine Francos, PLLC

(57) ABSTRACT

In the manufacture of a micromechanical device, a substrate, having a mask thereon, is etched using a flourine-containing etchant gas or vapour in the absence of a plasma through an opening in the mask to a desired depth to form a trench having a side wall and a base in the substrate. A layer of protecting substance is deposited on the exposed surfaces of the substrate and mask, and the protecting substance is then selectively removed from the base. The base is then etched using the fluorine-containing etchant.

13 Claims, 4 Drawing Sheets

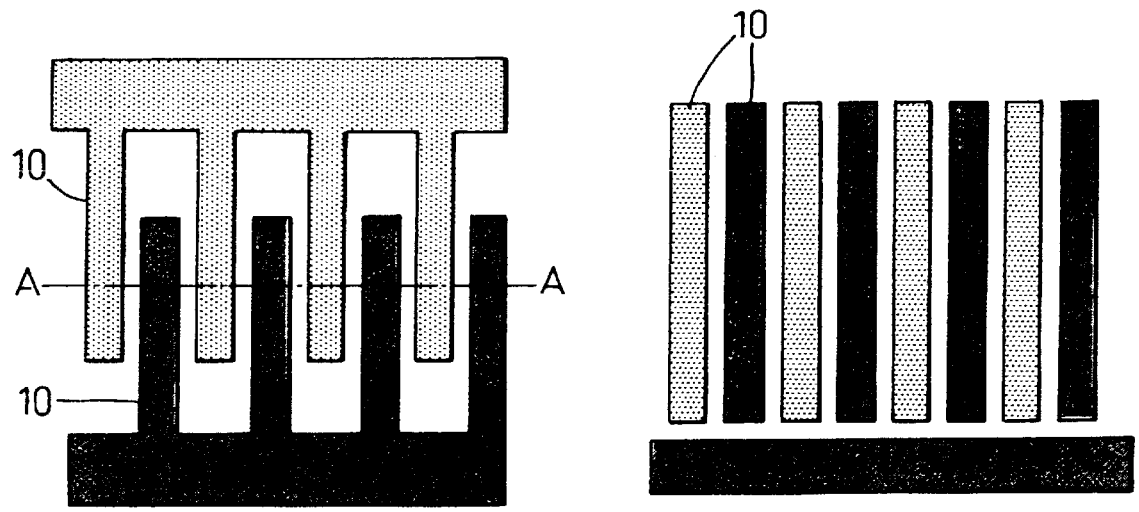
*Fig. 7*  *Fig. 8*
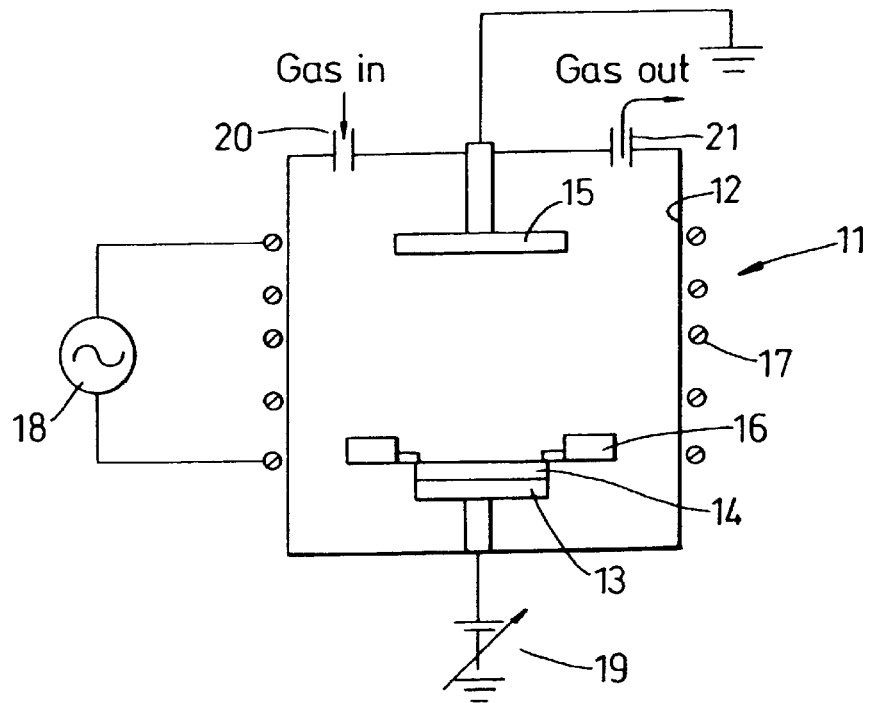
*Fig. 9*

METHOD AND APPARATUS FOR MANUFACTURING A MICROMECHANICAL DEVICE

The present invention relates to a method and apparatus for manufacturing a micromechanical device using a fluorine etchant source, for example xenon difluoride ($XeF_2$). Xenon difluoride is a dry isotropic gas phase etchant, which provides a gentle etch for silicon at low temperature. Xenon difluoride is usually supplied in the form of colourless crystals which sublime without decomposition. The sublimation pressure for $XeF_2$ is approximately 4 Torr.

A current method of manufacturing a micromechanical device uses the steps of anisotropic etching, mask removal, silicon oxide deposition, selective oxide etching, and isotropic etching of silicon with a $SF_6$ plasma and oxide strip. However, this method requires many steps which results in long cycle times and a high cost. Other methods etch down to a buried oxide layer of silicon dioxide and selectively stop the anisotropic silicon etch at that interface. The silicon oxide is then selectively removed by HF to release the silicon structures. However, this method requires the use of wafers having a buried oxide layer which are very costly as well as additional equipment for HF based etching. Furthermore, liquid HF etching itself has considerable potential for stiction issues.

According to a first aspect of the present invention, here is provided a method of manufacturing a micromechanical device comprising the steps of:

(a) etching a substrate, having a mask thereon, through an opening in the mask to a desired depth to form a trench having a side wall and a base in the substrate;

(b) depositing a layer of a protecting substance on the exposed surfaces of the substrate and mask;

(c) selectively removing the protecting substance from the base; and (d) etching the base using a fluorine-containing etchant.

The fluorine-containing etchant may be a gas or vapour used to etch the substrate in the absence of a plasma.

Preferably, the fluorine-containing etchant is $XeF_2$. However, other vapours such as $F_2$ or $ClF_3$ (which will either etch or enhance the etch rate of silicon in the gas phase) as discussed in our co-pending British Patent Application No. 9904925.6 may be equally applied either as a replacement to $XeF_2$, or in the form of a mixture, for example with $XeF_2$. Thus, whilst the use of $XeF_2$ is discussed below in detail, other gases could be used.

Conveniently, the mask may be provided with a plurality of openings therein.

The method may further comprise the step of removing the mask and remaining protecting substance. This removal may be by means of a plasma. The substrate is preferably formed of silicon.

In a preferred embodiment, the mask is deposited by a photolithographic process.

The substrate is preferably etched by substantially anisotropic etching. The anisotropic etching may conveniently be performed using the methods described in EP-A-0822582 and EP-A-0822584, the contents of which are incorporated herein by reference.

The use of $XeF_2$ in a method and apparatus for etching a workpiece are disclosed in British Patent Application No. 9709659.8, the contents of which are incorporated herein by reference.

The protecting substance may be of the form $C_YF_X$ (where X and Y may be any suitable value) such as $CF_X$ polymeric chains, where x may be 2. Thus, the protecting substance may be of the general formula $n(CF_2)$. One example may be cross-linked PTFE. The deposition may be performed by generating a plasma, for example an RF plasma, with an appropriate source gas, for example $C_4F_8$. In a preferred embodiment, a typical deposition thickness of the protecting substance is in the range of about 10 to 100 nm. Alternatively, the protecting substance may be of the form $C_YH_X$ such as $CH_X$ polymeric chains, where x may be 2. Thus, it may be of the general formula $n(CH_2)$. In this case the source gas may be $CH_4$, for example. Again X and Y may be any suitable value.

The protecting substance may be selectively removed from any or all of the surfaces other than the side wall and etching with the fluorine-containing etchant may take place on all resulting unprotected areas.

The protecting substance may selectively be removed by a plasma such as oxygen or (well known) mixtures with argon, helium, or nitrogen for example. The requirement for selective removal may be achieved by a suitable plasma process as known in the art.

The etching with the fluorine-containing etchant may be isotropic etching of the unprotected areas of the substrate.

According to a second aspect of the present invention, there is provided a device formed by the above method.

The device may be formed as a series of adjacent fingers separated by trenches. A fluorine-containing etchant, for example $XeF_2$, may be used to undercut such that the trenches are in communication.

According to a third aspect of the present invention, there is provided an apparatus for manufacturing a micromechanical device comprising:

(a) means for etching a substrate, having a mask thereon, to a desired depth;

(b) means for depositing a layer of a protecting substance on the exposed surfaces of the substrate and mask;

(c) means for selectively removing the protecting substance; and (d) means for providing a fluorine-containing etchant for etching the unprotected areas.

The means for depositing the protecting substance may be means for generating a plasma. The means for selectively removing the protecting substance preferably includes means for providing a suitable plasma.

In a preferred embodiment, the apparatus may further comprise means for removing the mask and the remaining protecting substance and this means may be a plasma source, preferably an oxygen plasma source.

Although the invention has been described above, it is to be understood that it includes any inventive combination of the features set out above or in the following description.

The invention may be performed in various ways and a specific embodiment will now be described, by way of example, with reference to the accompanying drawings in which:

FIG. 7 is a top view of inter-digitated silicon fingers formed by the method of the present invention;

FIG. 8 is a cross sectional view of FIG. 7 along the line A—A; and

FIG. 9 shows a schematic view of an apparatus of the present invention.

Figure 1:
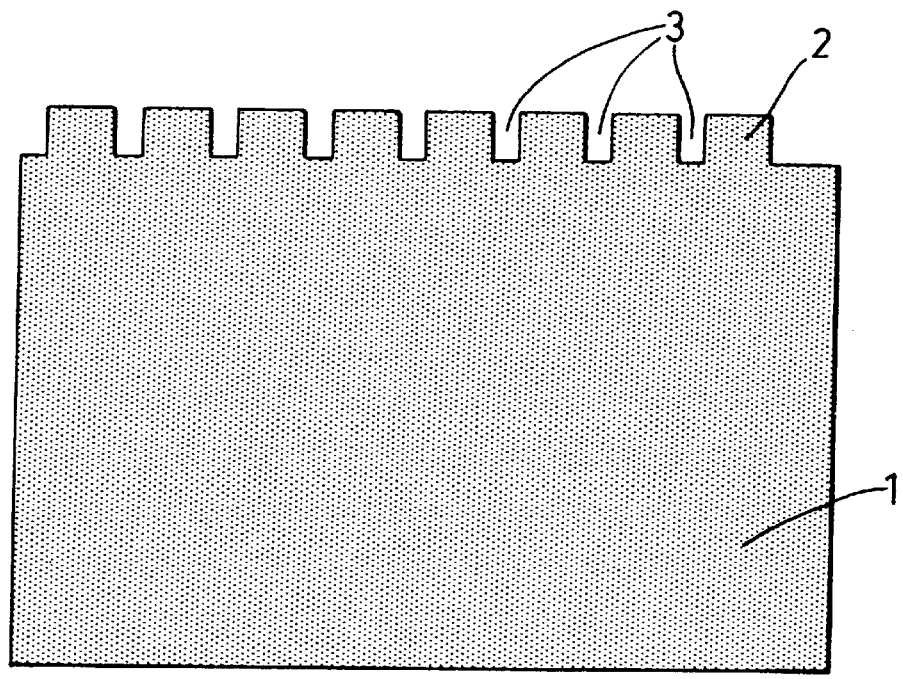
FIG. 1 is a cross section of a silicon substrate having a pattern photoresist.

FIG. 1 shows a silicon substrate 1 on which is a patterned photoresist (mask) 2. The silicon substrate 1 is patterned by the use of photolithographic processes. Between the parts of the photoresist 2 are channels 3.

Figure 2:
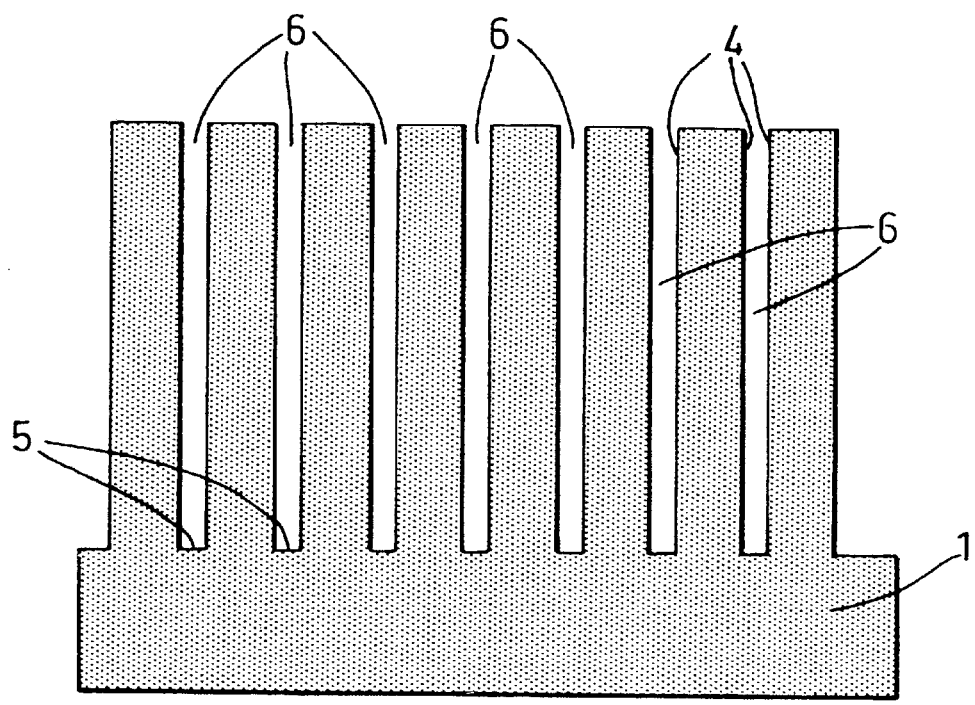
FIG. 2 is a cross section view corresponding to that in FIG. 1 in which the silicon has been etched.

As shown in FIG. 2, the silicon is then etched to a desired depth by anisotropic etching in a downward direction so that there is as little etching of the side walls of the formation as possible. The etching may be carried out by any suitable process. In this respect reference is made to EP-A-0822582 and EP-A-0822584. The etching leads to formation of side walls 4 and bases 5. The series of side walls 4 and bases 5 together form trenches 6.

Figure 3:
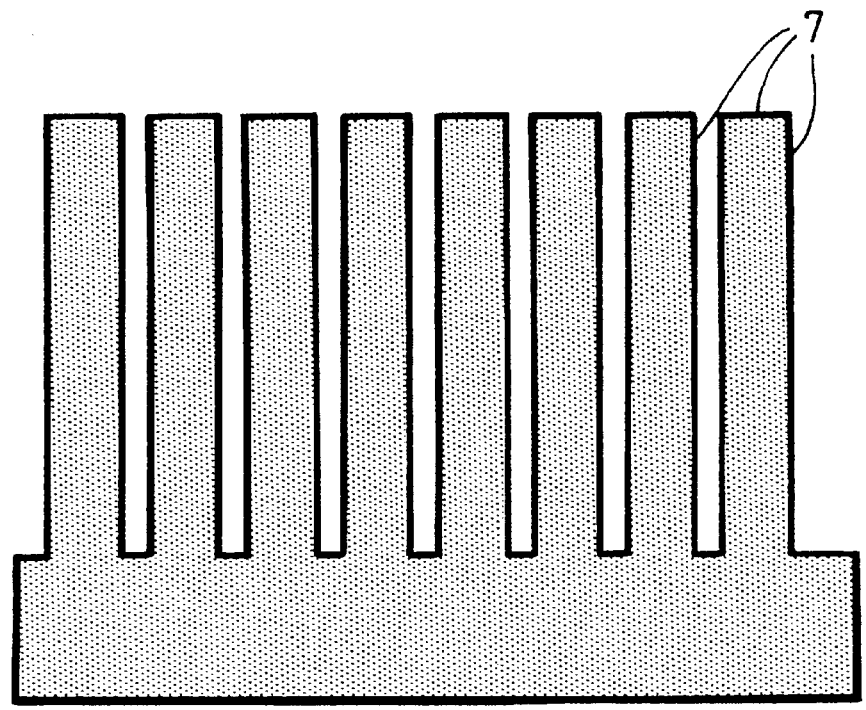
FIG. 3 shows a cross sectional view corresponding to FIGS. 1 and 2 in which a protecting layer has been deposited.

As shown in FIG. 3, a layer of a protecting substance is deposited on the exposed surfaces to a thickness of about 100 nm. The deposited layer is shown at 7. This layer is deposited in the process chamber by generating a RF plasma with the source gas being $C_4F_8$ and provides a layer of $C_YF_X$ as mentioned above. One example is thought to be a layer of cross-linked PTFE.

Figure 4:
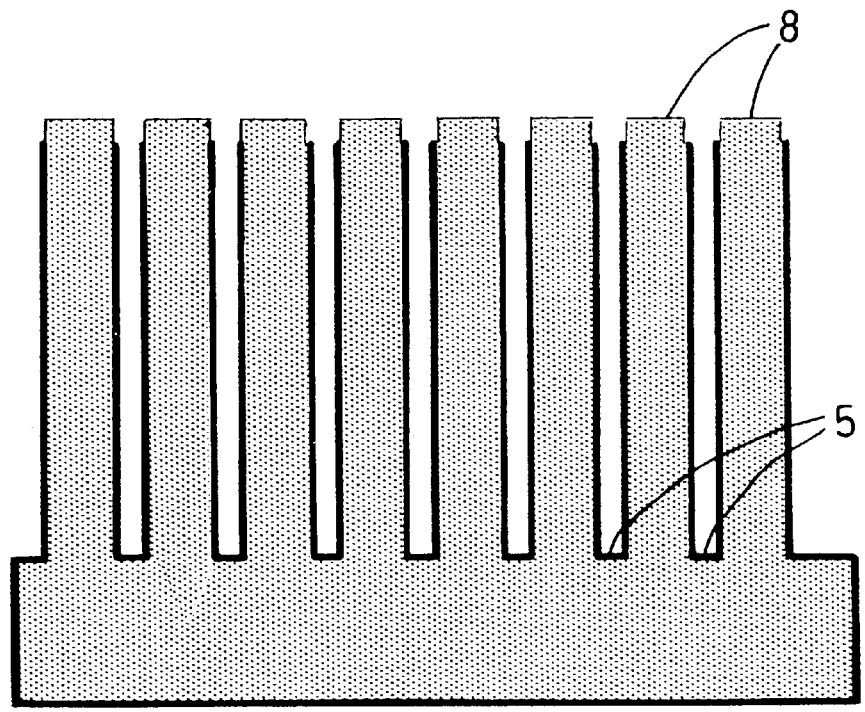
FIG. 4 shows a corresponding cross sectional view in which the protecting layer has been selectively removed.

Turning to FIG. 4, an argon/oxygen mixture selectively removes the $C_YF_X$ (for example the cross-linked PTFE) from the horizontal surfaces shown by upper surfaces 8 and bases 5. The requirement may be achieved by using, for example, low pressure reactive ion etching or inductively coupled plasma technique as mentioned above.

Figure 5:
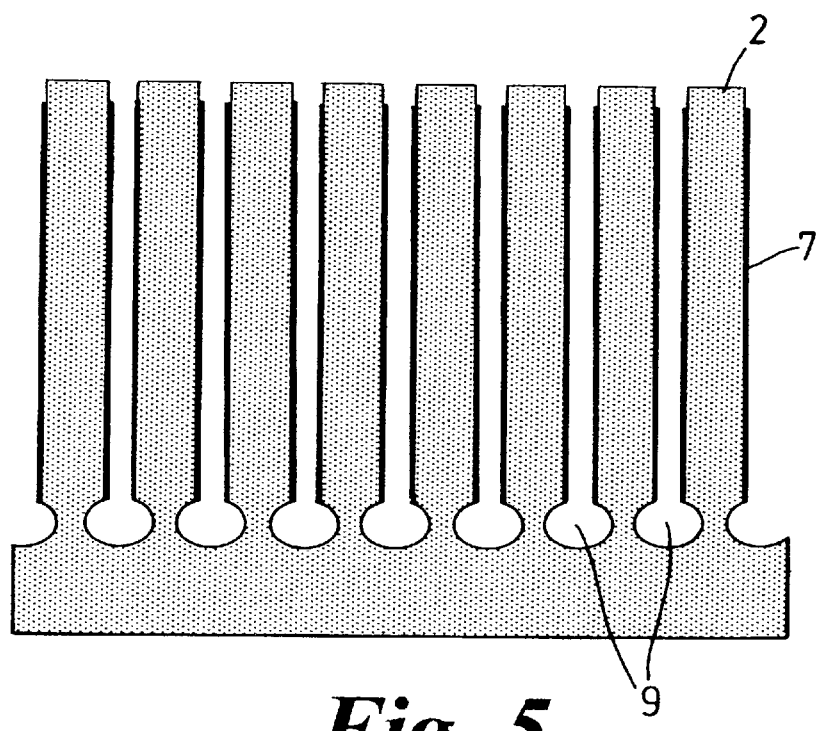
FIG. 5 shows a corresponding cross section view showing a partial etch of the substrate.

It is then possible to etch the unprotected silicon areas on the bases 5. FIG. 5 shows the result of a partial etch which leads to etches 9. In the present invention, $XeF_2$ is used to isotropically etch the unprotected silicon areas leading to the etches 9.

Figure 6:
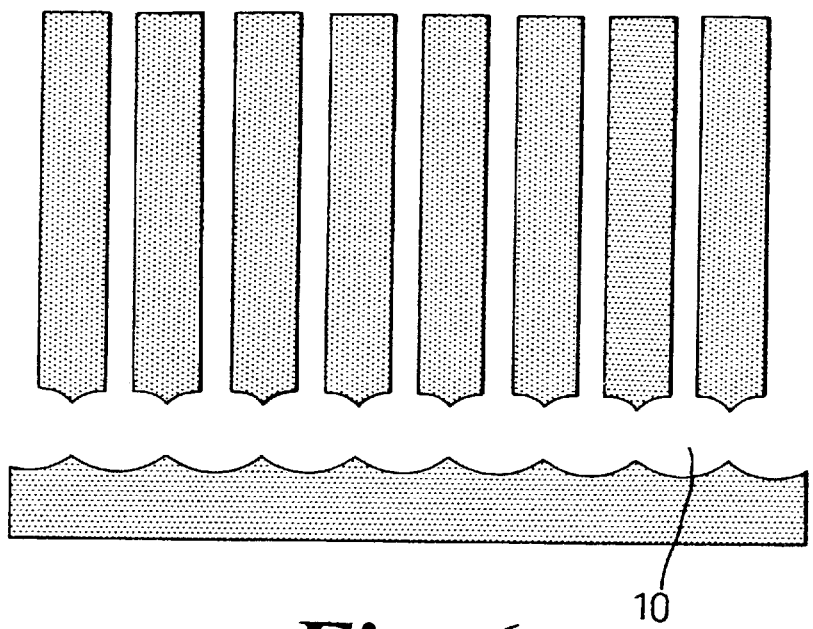
FIG. 6 shows a corresponding cross section view in which etching has been completed.

FIG. 6 shows the result of etching to completion by $XeF_2$ followed by an oxygen plasma to remove both the photoresist 2 and remaining deposited layer 7. This etching provides the completed etch indicated by 10.

The method described above provides a simple approach to releasing silicon microstructures after they have been formed by anisotropic etching. Thus, FIG. 5, as described above shows a structure in which the release process is happening and FIG. 6 shows a structure when released. The method may be carried out sequentially in the same process chamber as the anisotropic etch. Thus, all the steps may be carried out in the same process chamber.

In the sequence shown by FIGS. 1 to 6, an example structure of inter-digitated silicon fingers is produced. The method may be applied to either bulk or polysilicon based structures.

FIGS. 7 and 8 show the final form of the resulting silicon microstructure in which inter-digitated silicon fingers 10 are shown.

Whilst the microstructures resulting from the present invention have a number of applications, typical applications for such structures may be accelerometers and gyroscopes which are based upon capacitance sensing between the silicon fingers by means of anchoring one set of silicon fingers 10 and allowing the other set to move when force is applied, this movement being sensed by the change in capacitance.

FIG. 9 illustrates a reactor chamber 11 suitable for use in the present invention. Typically, a vacuum chamber 12 incorporates a support electrode 13 for receiving a substrate 14 and a further spaced electrode 15. The substrate 14 may be pressed against the support 13 by a clamp 16. The chamber 12 is surrounded by a coil 17 and fed by a RF source which is used to induce a plasma in the chamber 12 between electrodes 13 and 15. Alternatively a microwave power supply may be used to create the plasma. In both cases there is a need to create a plasma bias, which can be either RF or DC and can be connected to the support electrode 13 so as to influence the passage of ions from the plasma onto substrate 14. An example of such an adjustable bias means is indicated at 19. The chamber is provided with a gas inlet port 20 and an exhaust port 21.

What is claimed is:

1. A method of manufacturing a micromechanical device, comprising:
    (a) etching a substrate, having a mask thereon, using a flourine-containing etchant gas or vapour in the absence of a plasma through an opening in the mask to a desired depth to form a trench having a side wall and a base in the substrate;
    (b) depositing a layer of a protecting substance on the exposed surfaces of the substrate and mask;
    (c) selectively removing the protecting substance from the base; and
    (d) etching the base using a fluorine-containing etchant.

2. A method according to claim 1, wherein the fluorine-containing etchant is selected from $XeF_2$, $F_2$, $ClF_3$ or mixtures thereof.

3. A method according to claim 1, wherein the fluorine-containing etchant is $XeF_2$.

4. A method according to claim 1, further comprising the step of removing the mask and remaining protecting substance.

5. A method according to claim 1, wherein the protecting substance is a fluorocarbon polymer of the general formula $C_YF_X$, where X and Y are positive integers.

6. A method according to claim 5, wherein the protecting substance is of the general formula $n(CF_2)$, where n is a positive integer.

7. A method according to any one of the claim 1, wherein the protecting substance is of the form $C_YH_X$, where X and Y are positive integers.

8. A method according to claim 7, wherein the protecting substance is of the general formula $n(CH_2)$, wherein n is a positive integer.

9. A micromechanical device formed by the method of claim 1.

10. A micromechanical device according to claim 9, comprising a series of adjacent fingers separated by trenches.

11. A micromechanical device according to claim 10, wherein the trenches are in communication.

12. An apparatus for manufacturing a micromechanical device comprising:
    (a) means providing a flourine-containing etchant gas or vapour in the absence of a plasma for etching a substrate, having a mask thereon, to a desired depth;
    (b) means for depositing a layer of a protecting substance on the exposed surfaces of the substrate and mask;
    (c) means for selectively removing the protecting substance; and
    (d) means for providing the fluorine-containing etchant for etching the unprotected areas.

13. An apparatus according to claim 12, further comprising means for removing the mask and the remaining protecting substance.

* * * * *